US011573232B2

(12) United States Patent
Minagawa et al.

(10) Patent No.: US 11,573,232 B2
(45) Date of Patent: Feb. 7, 2023

(54) METHOD FOR CAPTURING SPECIFIC CELLS

(71) Applicants: SUMITOMO RUBBER INDUSTRIES, LTD., Kobe (JP); YAMAGATA UNIVERSITY, Yamagata (JP)

(72) Inventors: Yasuhisa Minagawa, Kobe (JP); Masaru Tanaka, Yonezawa (JP); Takashi Hoshiba, Yonezawa (JP); Haruka Emura, Yonezawa (JP)

(73) Assignees: SUMITOMO RUBBER INDUSTRIES, LTD., Kobe (JP); YAMAGATA UNIVERSITY, Yamagata (JP)

( * ) Notice: Subject to any disclaimer, the term of this patent is extended or adjusted under 35 U.S.C. 154(b) by 0 days.

(21) Appl. No.: 16/249,454

(22) Filed: Jan. 16, 2019

(65) Prior Publication Data
US 2019/0250150 A1 Aug. 15, 2019

(30) Foreign Application Priority Data

Feb. 14, 2018 (JP) .............................. JP2018-024118

(51) Int. Cl.
*G01N 33/574* (2006.01)
*B01D 21/26* (2006.01)
*G01N 33/50* (2006.01)
*G01N 33/539* (2006.01)
*G01N 33/537* (2006.01)
*G01N 35/00* (2006.01)

(52) U.S. Cl.
CPC ......... *G01N 33/574* (2013.01); *B01D 21/262* (2013.01); *G01N 33/5002* (2013.01); *G01N 33/5091* (2013.01); *G01N 33/539* (2013.01); *G01N 33/5375* (2013.01); *G01N 2035/00495* (2013.01)

(58) Field of Classification Search
CPC ............ G01N 33/5375; G01N 33/539; G01N 33/571; G01N 2035/00495; G01N 33/5002; G01N 33/5091; G01N 33/574
See application file for complete search history.

(56) References Cited

U.S. PATENT DOCUMENTS

| 5,202,025 | A | 4/1993 | Onishi | |
|---|---|---|---|---|
| 7,211,433 | B1 | 5/2007 | Dahm et al. | |
| 9,372,136 | B2* | 6/2016 | Kanbara | G01N 1/405 |
| 10,941,374 | B2 | 3/2021 | Minagawa et al. | |
| 2002/0155617 | A1 | 10/2002 | Pham et al. | |
| 2003/0190405 | A1* | 10/2003 | Bowers | C08F 246/00 427/2.1 |
| 2006/0008807 | A1 | 1/2006 | O'Hara et al. | |
| 2006/0160066 | A1 | 7/2006 | Bhatia | |
| 2007/0099207 | A1 | 5/2007 | Fuchs et al. | |
| 2008/0008736 | A1 | 1/2008 | Glauser | |
| 2008/0038841 | A1 | 2/2008 | Ezoe et al. | |
| 2009/0186341 | A1 | 7/2009 | Dahm | |
| 2010/0261159 | A1 | 10/2010 | Hess et al. | |
| 2011/0123414 | A1 | 5/2011 | Ahern et al. | |
| 2012/0077246 | A1 | 3/2012 | Hong et al. | |
| 2012/0108468 | A1 | 5/2012 | Keselowsky et al. | |
| 2012/0156698 | A1 | 6/2012 | Jendoubi | |
| 2013/0059288 | A1 | 3/2013 | Dankbar et al. | |
| 2013/0071916 | A1 | 3/2013 | Frutos et al. | |
| 2013/0072402 | A1 | 3/2013 | Takamura et al. | |
| 2013/0210140 | A1 | 8/2013 | Burns et al. | |
| 2014/0158604 | A1 | 6/2014 | Chammas et al. | |
| 2014/0299539 | A1 | 10/2014 | Takai et al. | |
| 2014/0335610 | A1 | 11/2014 | Fukumori et al. | |
| 2015/0017221 | A1 | 1/2015 | Hayashi et al. | |
| 2015/0285786 | A1 | 10/2015 | Hahn et al. | |
| 2016/0011192 | A1 | 1/2016 | Wagner | |
| 2016/0069861 | A1 | 3/2016 | Santore et al. | |
| 2016/0116477 | A1 | 4/2016 | Hoffmann et al. | |
| 2016/0122488 | A1 | 5/2016 | Minagawa | |
| 2016/0136662 | A1 | 5/2016 | Nakanishi et al. | |
| 2016/0168294 | A1 | 6/2016 | Hayashi et al. | |
| 2016/0223521 | A1 | 8/2016 | Okamoto et al. | |
| 2016/0291019 | A1 | 10/2016 | Yoon et al. | |
| 2017/0113218 | A1 | 4/2017 | Chen et al. | |

(Continued)

FOREIGN PATENT DOCUMENTS

| CN | 104039949 A | 9/2014 |
|---|---|---|
| CN | 105263995 A | 1/2016 |

(Continued)

OTHER PUBLICATIONS

Yao et al. Functional analysis of single cells identifies a rare subset of circulating tumor cells with malignant trait. Integr Biol (Camb) 6(4): 388-398 (Apr. 2014).*
He et al, "Quantitation of Circulating Tumor Cells in Blood Samples from Ovarian and Prostate Cancer Patients Using Tumor-Specific Fluorescent Ligands", International Journal of Cancer, vol. 123, 2008, pp. 1968-1973.
Klöckner et al., "Advances in shaking technologies," Trends in Biotechnology, vol. 30, No. 6, Jun. 2012, pp. 307-314.
Hoshiba et al., "Adhesion-Based Simple Capture and Recovery of Cirulating Tumor Cells Using a Blood-Compatible and Thermo-Responsive Polymer-Coated Substrate," RSC Advances, vol. 6, , 2016 (Published on Sep. 13, 2015), pp. 89103-89112.

(Continued)

*Primary Examiner* — Gailene Gabel
(74) *Attorney, Agent, or Firm* — Birch, Stewart, Kolasch & Birch, LLP

(57) ABSTRACT

The present invention provides a method for capturing specific cells (e.g. many types of cancer cells, including cancer cells not expressing EpCAM), and a method for analysis of specific cells involving the method. Included is a method for capturing specific cells present in blood or biological fluid, the method including: agglutinating blood cells in sampled blood or biological fluid; centrifuging the resulting blood or biological fluid; and then capturing specific cells therefrom onto a hydrophilic polymer layer.

7 Claims, 1 Drawing Sheet

(56) References Cited

U.S. PATENT DOCUMENTS

| | | |
|---|---|---|
| 2017/0225166 A1 | 8/2017 | Toner et al. |
| 2017/0267960 A1 | 9/2017 | Tsukada et al. |
| 2017/0304823 A1 | 10/2017 | Sparks et al. |
| 2018/0087017 A1 | 3/2018 | Minagawa et al. |
| 2018/0088105 A1* | 3/2018 | Minagawa ......... G01N 33/5005 |
| 2018/0088106 A1 | 3/2018 | Minagawa et al. |
| 2018/0201892 A1 | 7/2018 | Gomi et al. |
| 2019/0048113 A1 | 2/2019 | Hayashi et al. |
| 2019/0054123 A1* | 2/2019 | Kanai ..................... A61K 35/28 |
| 2019/0170741 A1 | 6/2019 | Alix-Panabieres et al. |
| 2019/0233555 A1 | 8/2019 | Minagawa et al. |
| 2019/0250149 A1* | 8/2019 | Minagawa ......... G01N 33/5091 |
| 2019/0250151 A1* | 8/2019 | Minagawa ........... B01D 21/262 |
| 2020/0056137 A1 | 2/2020 | Anzai et al. |
| 2020/0056138 A1 | 2/2020 | Anzai et al. |
| 2020/0056154 A1 | 2/2020 | Anzai et al. |
| 2020/0056155 A1 | 2/2020 | Anzai et al. |

FOREIGN PATENT DOCUMENTS

| | | |
|---|---|---|
| CN | 105636615 A | 6/2016 |
| EP | 0 225 703 A2 | 6/1987 |
| EP | 1655354 A2 | 5/2006 |
| EP | 1 905 824 A1 | 4/2008 |
| EP | 2720039 A1 | 4/2014 |
| EP | 3 244 206 A1 | 11/2017 |
| EP | 3 301 443 A1 | 4/2018 |
| EP | 3 301 444 A1 | 4/2018 |
| EP | 3301443 A1 | 4/2018 |
| EP | 3 527 985 A1 | 8/2019 |
| EP | 3 527 986 A1 | 8/2019 |
| GB | 2472321 A | 2/2011 |
| JP | 2-10160 A | 1/1990 |
| JP | 3-110473 A | 5/1991 |
| JP | 7-83923 A | 3/1995 |
| JP | 2002-536635 A | 10/2002 |
| JP | 2003-501629 A | 1/2003 |
| JP | 2004-522937 A | 7/2004 |
| JP | 2005-82538 A | 3/2005 |
| JP | 2005-188987 A | 7/2005 |
| JP | 2005-523981 A | 8/2005 |
| JP | 2006-109757 A | 4/2006 |
| JP | 2007-78665 A | 3/2007 |
| JP | 2007-515654 A | 6/2007 |
| JP | 2007-256268 A | 10/2007 |
| JP | 2008-529541 A | 8/2008 |
| JP | 2010/509570 A | 3/2010 |
| JP | 2012-105579 A | 6/2012 |
| JP | 2012-522217 A | 9/2012 |
| JP | 2013-500496 A | 1/2013 |
| JP | 2013-174616 A | 9/2013 |
| JP | 2014-105159 A | 6/2014 |
| JP | 2015-514396 A | 5/2015 |
| JP | 2015-224332 A | 12/2015 |
| JP | 2016-514950 A | 5/2016 |
| JP | 2016-131561 A | 7/2016 |
| JP | 2016-158019 A | 9/2016 |
| JP | 2017-83247 A | 5/2017 |
| JP | 2017-116511 A | 6/2017 |
| JP | 2017-523431 A | 8/2017 |
| JP | 2017-181096 A | 10/2017 |
| JP | 2018-59901 A | 4/2018 |
| RU | 2 477 981 C2 | 3/2013 |
| WO | WO 99/42608 A1 | 8/1999 |
| WO | WO 00/20921 A1 | 4/2000 |
| WO | WO 00/73794 A2 | 12/2000 |
| WO | WO 02/20825 A1 | 3/2002 |
| WO | WO 03/093357 A1 | 11/2003 |
| WO | WO 2005/064347 A1 | 7/2005 |
| WO | WO 2006/108087 A2 | 10/2006 |
| WO | WO 2007/092028 A2 | 8/2007 |
| WO | WO 2008/057437 A2 | 5/2008 |
| WO | WO 2010/111388 A2 | 9/2010 |
| WO | WO 2011/017094 A2 | 2/2011 |
| WO | WO 2011/157805 A | 12/2011 |
| WO | WO 2011/161480 A1 | 12/2011 |
| WO | WO 2012/108087 A1 | 8/2012 |
| WO | WO 2013/112541 A2 | 8/2013 |
| WO | WO 2013/134788 A1 | 9/2013 |
| WO | WO 2014/117021 A2 | 7/2014 |
| WO | WO 2014/203668 A1 | 12/2014 |
| WO | WO 2015/012315 A1 | 1/2015 |
| WO | WO 2015/046557 A1 | 4/2015 |
| WO | WO 2015/137259 A1 | 9/2015 |
| WO | WO 2015/178413 A1 | 11/2015 |
| WO | WO 2016/103002 A1 | 6/2016 |
| WO | WO 2016/115537 A2 | 7/2016 |
| WO | WO 2017/087032 A1 | 5/2017 |
| WO | WO 2017/178662 A1 | 10/2017 |

OTHER PUBLICATIONS

Khoo et al., "Liquid Biopsy and Therapeutic Response: Circulating Tumor Cell Cultures for Evaluation of Anticancer Treatment," Sci. Adv., vol. 2, e1600274, Jul. 13, 2016, pp. 1-15 (total 16 pages).

Vona et al, "Isolation by Size of Epithelial Tumor Cells, A New Method for the Immunomorphological and Molecular Characterization of Circulating Tumor Cells," American Journal of Pathology, vol. 156, No. 1, Jan. 2000, pp. 57-63.

Williams, "Circulating Tumor Cells," PNAS, vol. 110, No. 13, Mar. 26, 2013, pp 4861.

Yao et al., "Functional Analysis of Single Cells Identifies a Rare Subset of Circulating Tumor Cells with Malignant Traits," Integr Biol (Camb), vol. 6, No. 4, Apr. 2014, pp. 368-398 (total 20 pages).

Hoshiba et al., "Blood-compatible poly(2-methoxyethyl acrylate) for the adhesion and proliferation of lung cancer cells toward the isolation and analysis of circulating tumor cells," Journal of Bioactive and Compatible Polymers, vol. 31(4) (2016), pp. 361-372.

Gach et al., "Micropallet Arrays for the Capture, Isolation and Culture of Circulating Tumor Cells From Whole Blood of Mice Engrafted With Primary Human Pancreatic Adenocarcinoma", Biosensors and Bioelectronics, vol. 54, 2014, (Available online Nov. 18, 2013), pp. 476-483.

Nel et al., "Circulating tumor cell composition and outcome in patients with solid tumors," International Journal of Clinical Pharmacology and Therapeutics, vol. 52, No. 1/2014 pp. 74-75, e-pub: Nov. 11, 2013.

"Improved Recovery of Cell-Derived Exosomes by MPC Polymer Coatings," Nippon Genetics Co., Ltd, vol. 9, 2018, with a concise explanation of the relevance.

Fernandez et al., "TP53 mutations detected in circulating tumor cells present in the blood of metastatic triple negative breast cancer patients," Breast Cancer Research, vol. 16, No. 445, 2014, pp. 1-11.

Khoo et al., Oncotarget, vol. 6, No. 17, May 6, 2015, pp. 15578-15593.

Miltenyi Biotec, "Isolation of mononuclear cells from human peripheral blood by density gradient centrifugation," MACS, 2008, pp. 1-2.

Sansyo General Catalogue, "Tissue Culture and Filtration Ware, IWAKI Tissue Culture Ware," 2015 pp. 7 (total 2 pages).

Takai, "Bio-interface for Highly Sensitive Blood Analysis Chip," Surface Science, vol. 32, No. 9, 2911, pp. 575-580, with English abstract.

Xu et al., "Optimization and Evaluation of a Novel Size Based Circulating Tumor Cell Isolation System," PLOS One, Sep. 23, 2015, pp. 1-23.

Yamamura et al., "Accurate Detection of Carcinoma Cells by Use of a Cell Microarray Chip," Plos One, vol. 7, Issue 3, Mar. 1, 2012, e32370 (9 pages total).

Rosenberg et al., "Comparison of Two Density Gradient Centrifugation Systems for the Enrichment of Disseminated Tumor Cells in Blood," Cytometry, vol. 49, 2002, pp. 150-158.

Vissers et al., "Rapid purification of human peripheral blood monocytes by centrifugation through Ficoll-Hypaque and Sepracell-MN," Journal of Immunological Methods, vol. 110, 1988, pp. 203-207.

* cited by examiner

A-A cross-sectional view

METHOD FOR CAPTURING SPECIFIC CELLS

TECHNICAL FIELD

The present invention relates to a method for capturing specific cells (e.g. cancer cells present in blood or biological fluid) from blood or biological fluid, and a method for analysis of specific cells.

BACKGROUND ART

When cancer cells are formed, they are known to appear in due course in blood or biological fluid. Such cancer cells in blood are called "circulating tumor cells (CTCs)". Thus, it can be expected that the circulating tumor cells may be analyzed, e.g. to evaluate the cancer-treating effect, predict prognosis life expectancy, predict the effect of anticancer drugs before administration, or examine treatment methods based on genetic analysis of cancer cells.

However, a problem exists in that since the number of circulating tumor cells is very small (several to hundreds of cells/1 mL of blood), such cancer cells are difficult to capture.

For example, the CellSearch System is known as a technique for capturing circulating tumor cells. This technique, which involves an antigen-antibody reaction (capture by EpCAM antibody), can only capture cancer cells expressing EpCAM, and the type of cancer cells that can be captured is limited.

CITATION LIST

Patent Literature

Patent Literature 1: JP 2005-523981 T

SUMMARY OF INVENTION

Technical Problem

The present invention aims to solve the problem and provide a method for capturing specific cells (e.g. many types of cancer cells, including cancer cells not expressing EpCAM), and a method for analysis of specific cells involving the method.

Solution to Problem

The present invention relates to a method for capturing specific cells present in blood or biological fluid, the method including: agglutinating blood cells in sampled blood or biological fluid; centrifuging the resulting blood or biological fluid; and then capturing specific cells therefrom onto a hydrophilic polymer layer.

The specific cells are preferably cancer cells.

In the method for capturing specific cells, the sampled blood or biological fluid is preferably diluted before the agglutination and the centrifugation.

Preferably, a buffer solution or a liquid medium is used for the dilution.

The agglutinating blood cells preferably includes an antigen-antibody reaction.

The hydrophilic polymer layer is preferably formed of at least one hydrophilic polymer selected from the group consisting of poly(meth)acryloylmorpholine and polymers represented by the following formula (I):

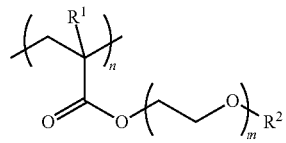

wherein $R^1$ represents a hydrogen atom or a methyl group, $R^2$ represents an alkyl group, m represents 1 to 5, and n represents the number of repetitions.

The hydrophilic polymer layer is preferably formed of a copolymer of at least one hydrophilic monomer selected from the group consisting of (meth)acryloylmorpholine and compounds represented by the following formula (I-1):

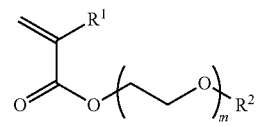

wherein $R^1$, $R^2$, and m are as defined above, with an additional monomer.

The hydrophilic polymer layer preferably has a thickness of 10 to 500 nm.

Another aspect of the present invention relates to a method for analysis of specific cells, including capturing specific cells from blood or biological fluid by the method for capturing specific cells, and analyzing the specific cells.

Advantageous Effects of Invention

The method for capturing specific cells present in blood or biological fluid according to the present invention includes agglutinating blood cells in sampled blood or biological fluid, centrifuging the resulting blood or biological fluid, and then capturing specific cells therefrom onto a hydrophilic polymer layer. Such a method can effectively capture specific cells (e.g. many types of cancer cells, including cancer cells not expressing EpCAM). Thus, for example, it is possible to sufficiently capture specific cells such as cancer cells from blood or biological fluid and further to reduce adhesion or attachment of blood cells including red blood cells, white blood cells, and platelets, thereby selectively capturing the specific cells.

DESCRIPTION OF EMBODIMENTS

Figure 1A:
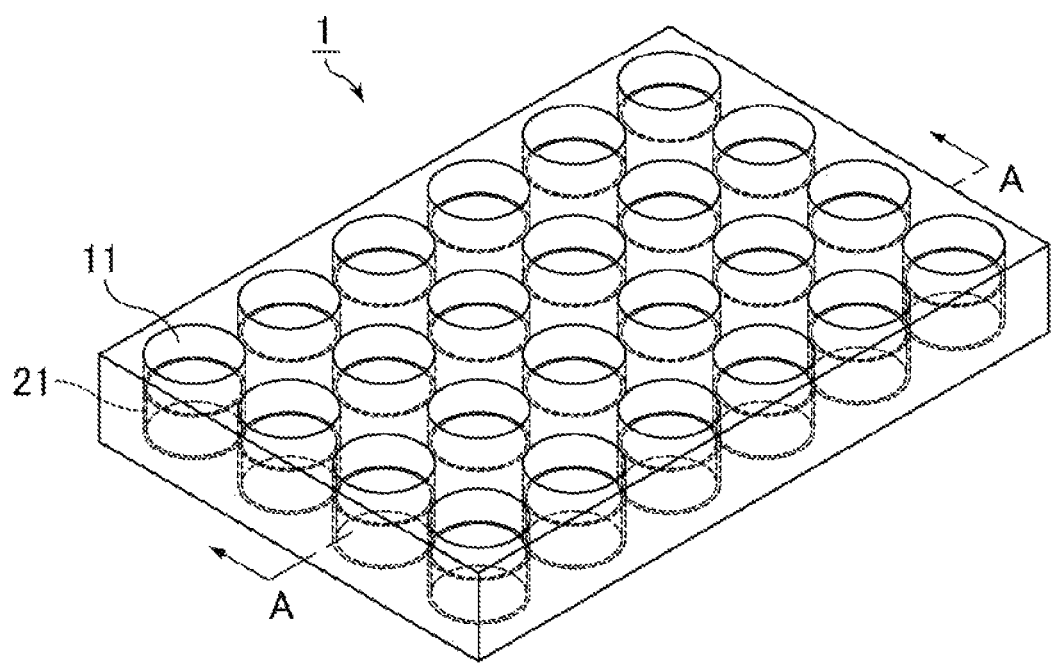
FIG. 1 shows exemplary schematic views of a multi-well plate having wells with a hydrophilic polymer layer formed thereon.

The present invention provides a method for capturing specific cells present in blood or biological fluid. The method includes: agglutinating blood cells in sampled blood or biological fluid; centrifuging the resulting blood or biological fluid; and then capturing specific cells therefrom onto a hydrophilic polymer layer.

Specifically, according to the present method, blood cells in blood or biological fluid sampled from, e.g., the body may be first agglutinated, and then the resulting blood or biological fluid may be centrifuged to prepare a sample having blood cell levels lower than the sampled blood or biological fluid. Thereafter, the sample may be contacted with a hydrophilic polymer layer to capture specific cells such as cancer cells in the sample. In particular, such a method provides improved separation of white blood cells and the like and reduction in the loss of specific cells such as cancer cells (the loss due to the specific cells being incorporated into the fraction of red blood cells and the like) as compared to when blood cells are not agglutinated. Thus, as the cell adhesion-inhibiting effect of blood cells and the like is reduced, specific cells exhibit their inherent ability to adhere to hydrophilic polymers. Therefore, the present method provides greatly improved capture of specific cells such as cancer cells and reduced capture of blood cells, whereby an effect which could never be produced when blood cells are present at high levels can be achieved in selectively capturing specific cells such as cancer cells.

For example, first, blood cells in sampled blood or biological fluid may be agglutinated by, for example, a method that includes binding and agglutinating red blood cells and white blood cells via an antigen-antibody reaction; then the blood cells such as red blood cells, white blood cells, and platelets, and the like in the blood or biological fluid may be separated (removed) by centrifugation to prepare a sample containing them at reduced levels; and subsequently the sample may be contacted with a hydrophilic polymer layer to selectively capture specific cells. Thus, the tumor cells and the like in the blood or biological fluid can be effectively captured onto the hydrophilic polymer layer. Then, it can be expected that by counting the number of captured tumor cells and the like, one can determine the number of tumor cells and the like in the blood or biological fluid, e.g. in order to evaluate the cancer-treating effect. Moreover, the captured tumor cells and the like may be cultured and then used to determine the effect of drugs such as anticancer drugs. This allows us to determine the effect of drugs such as anticancer drugs ex vivo before administration, and also helps to screen drugs such as anticancer drugs.

Examples of the specific cells used in the method for capturing specific cells include cancer cells (any cancer cells, including cancer cells not expressing EpCAM). Examples of the cancer cells include circulating tumor cells (CTCs).

The method for capturing specific cells includes first agglutinating blood cells in sampled blood or biological fluid.

The blood cells may be agglutinated by any method capable of causing this agglutination. Among such methods, those based on antigen-antibody reactions are suitable. Specifically, agglutination reactions such as hemagglutination may be suitably used.

When the blood cells in the blood or biological fluid are agglutinated via hemagglutination to prepare a sample containing agglutinates in the agglutination step, the agglutinates including blood cells can be removed by the subsequent centrifugation of the sample. Thus, the high levels of specific cells (e.g. cancer cells) remaining in the sample can be effectively captured onto the hydrophilic polymer layer.

The agglutination of blood cells may be suitably carried out using, for example, an antibody reagent for agglutinating red and white blood cells (an antibody composition for agglutinating red and white blood cells). In spite of the fact that some white blood cells having specific gravities close to the specific cells such as cancer cells can be poorly separated by centrifugation, when red blood cells and white blood cells are bound and agglutinated via an antigen-antibody reaction using the antibody composition, the specific cells can be well separated not only from red blood cells, platelets, and the like having specific gravities different from the specific cells, but also from white blood cells. Thus, it is possible to further improve adhesion and capture of the specific cells.

The method for capturing specific cells may include, prior to the agglutination of blood cells, an additional pretreatment to reduce protein levels in the blood or biological fluid. The additional pretreatment to reduce protein levels in the blood or biological fluid may be carried out, for example, by diluting the sampled blood or biological fluid. The dilution may be performed using a buffer solution such as a phosphate buffered saline (PBS) having the same pH as human blood (about 7.4) or a liquid medium such as Dulbecco's modified eagle's medium (DMEM). Specifically, it may be carried out by diluting the sampled blood or biological fluid with a buffer solution, or adding the sampled blood or biological fluid to a liquid medium for dilution, to obtain protein levels lower than the sampled blood or biological fluid.

In the method for capturing specific cells, after the additional pretreatment is optionally performed, blood cells may be agglutinated, followed by centrifugation. The centrifugation removes agglutinated blood cells in the sample.

The centrifugation process is preferably carried out at a centrifugal force of 200 to 3000 G (×g). A centrifugal force of 200 G or higher provides improved separation of blood cells and reduction in the loss of specific cells (the loss due to the specific cells being incorporated into the fraction of red blood cells and the like), thereby being effective in selectively capturing specific cells. A centrifugal force of 3000 G or lower can result in reduced stress on specific cells, thereby maintaining their original nature. The centrifugal force is more preferably 300 to 2800 G, still more preferably 400 to 2500 G.

The duration and temperature of the centrifugation may be appropriately selected, e.g. in view of the ability to separate blood cells. For example, the centrifugation may be performed for 1 to 120 minutes, preferably 1 to 60 minutes, at 2 to 40° C., preferably 3 to 30° C. The centrifugation may be carried out by known techniques, such as using a known centrifugal separator.

In the centrifugation process, the sampled blood or biological fluid may be centrifuged, followed by removing the supernatant containing platelets to prepare a sample having a platelet level lower than the sampled blood or biological fluid. Moreover, the sampled blood or biological fluid may be centrifuged, followed by separating an intermediate mononuclear cell layer to separate and remove red blood cells and platelets, thereby preparing a sample with an increased level of specific cells such as cancer cells.

In the method for capturing specific cells, the centrifugation process is followed by capturing the specific cells onto a hydrophilic polymer layer.

The hydrophilic polymer layer (the layer formed of a hydrophilic polymer) may be formed on a certain substrate. Examples of the substrate include acrylic resins (polyacrylic resins) such as polymethyl acrylate, polymethyl methacrylate, polyacrylic acid, and polymethacrylic acid; cycloolefin resins (polycycloolefins); carbonate resins (polycarbonates); styrene resins (polystyrenes); polyester resins such as polyethylene terephthalate (PET); polydimethylsiloxanes; and glass such as soda-lime glass and borosilicate glass.

The hydrophilic polymer layer (the layer formed of a hydrophilic polymer) preferably has a thickness of 10 to 500 nm, more preferably 30 to 400 nm, still more preferably 50 to 350 nm. When the thickness is adjusted within the range indicated above, selective capture of cancer cells and low adsorption of other proteins and cells can be well achieved.

The hydrophilic polymer may be appropriately selected from polymers having hydrophilicity. For example, it may be a homopolymer or copolymer of one or two or more hydrophilic monomers, or a copolymer of one or two or more hydrophilic monomers with an additional monomer. Examples of such homopolymers and copolymers include polyacrylic acid, polyacrylic acid esters, polymethacrylic acid, polymethacrylic acid esters, polyacryloylmorpholine, polymethacryloylmorpholine, polyacrylamide, and polymethacrylamide.

The hydrophilic monomers may be any monomer containing a hydrophilic group. Examples of the hydrophilic group include known hydrophilic groups such as an amide group, a sulfuric acid group, a sulfonic acid group, a carboxylic acid group, a hydroxyl group, an amino group, and an oxyethylene group.

Specific examples of the hydrophilic monomers include (meth)acrylic acid, (meth)acrylic acid esters (e.g. alkoxyalkyl (meth)acrylates such as methoxyethyl (meth)acrylate, and hydroxyalkyl (meth)acrylates such as hydroxyethyl (meth)acrylate), (meth)acrylamide, and (meth)acrylamide derivatives containing cyclic groups (e.g., (meth)acryloylmorpholine). Preferred among these are (meth)acrylic acid, (meth)acrylic acid esters, alkoxyalkyl (meth)acrylates, and (meth)acryloylmorpholine, with alkoxyalkyl (meth) acrylates being more preferred, with 2-methoxyethyl acrylate being particularly preferred.

The additional monomer may be appropriately selected as long as it does not inhibit the effects of the hydrophilic polymer. Examples include aromatic monomers such as styrene, vinyl acetate, and N-isopropylacrylamide which can impart temperature responsiveness.

In particular, the hydrophilic polymer is preferably at least one selected from the group consisting of poly(meth)acryloylmorpholine and polymers represented by the following formula (I):

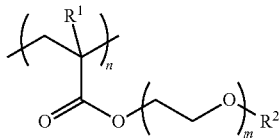
(I)

wherein $R^1$ represents a hydrogen atom or a methyl group, $R^2$ represents an alkyl group, m represents 1 to 5, and n represents the number of repetitions.

The alkyl group represented by $R^2$ preferably has 1 to 10 carbon atoms, more preferably 1 to 5 carbon atoms. In particular, $R^2$ is particularly preferably a methyl group or an ethyl group. The symbol m is preferably 1 to 3. The symbol n (number of repeating units) is preferably 15 to 1500, more preferably 40 to 1200.

Alternatively, the hydrophilic polymer may also suitably be a copolymer of at least one hydrophilic monomer selected from the group consisting of (meth)acryloylmorpholine and compounds represented by the formula (I-1) below with an additional monomer.

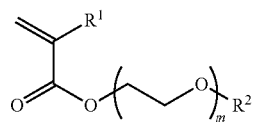
(I-1)

In formula (I-1), $R^1$, $R^2$, and m are as defined above.

The surface of the hydrophilic polymer layer preferably at least partially (partially or entirely) has a contact angle with water of 25° to 75°, more preferably 35° to 75°, still more preferably 35° to 70°. When the hydrophilic polymer layer has such a predetermined contact angle with water, the effects of the present invention can be well achieved.

The hydrophilic polymer layer may be formed by dissolving or dispersing a hydrophilic polymer in any solvent to prepare a hydrophilic polymer solution or dispersion, and entirely or partially coating the surface of a substrate with the hydrophilic polymer solution or dispersion by a known method, such as (1) by injecting the hydrophilic polymer solution or dispersion into the substrate surface (the recess of the substrate) and retaining and drying it for a predetermined time, or (2) by applying (spraying) the hydrophilic polymer solution or dispersion to the substrate surface and retaining and drying it for a predetermined time. Thus, a substrate provided with a polymer layer formed of a hydrophilic polymer can be prepared. Then, the substrate provided with a hydrophilic polymer layer may be combined with other components as needed, to prepare an apparatus capable of analyzing specific cells.

The solvent, injection method, application (spraying) method, and other conditions may be conventionally known materials or methods.

The retention/drying time in the method (1) or (2) may be selected appropriately according to the size of the substrate, the type of liquid introduced, and other factors. The retention time is preferably five minutes to ten hours, more preferably ten minutes to five hours, still more preferably 15 minutes to two hours. The drying is preferably performed at room temperature (about 23° C.) to 80° C., more preferably at room temperature to 50° C. Moreover, the drying may be carried out under reduced pressure. Furthermore, the hydrophilic polymer solution or dispersion may be retained for a certain period of time, optionally followed by discharging the excess solution or dispersion before drying.

The solvent may be any solvent that can dissolve the hydrophilic polymer and may be selected appropriately according to the hydrophilic polymer used. Examples include water, organic solvents, and solvent mixtures thereof. Examples of the organic solvents include alcohols such as methanol, ethanol, n-propanol, i-propanol, and methoxypropanol, ketones such as acetone and methyl ethyl ketone, tetrahydrofuran, acetonitrile, ethyl acetate, and toluene.

In the method for capturing specific cells, the sample (sample having lower blood cell levels) prepared by subjecting blood or biological fluid to agglutination of blood cells and centrifugation may be contacted with the substrate provided with a hydrophilic polymer layer to capture the specific cells. Contacting the sample with the hydrophilic polymer layer may be carried out by any method capable of this contact, such as by injecting or applying (spraying) the sample.

By contacting the sample with the hydrophilic polymer layer, the specific cells present in the sample can be captured onto the hydrophilic polymer layer while reducing adsorption of blood cells and the like. Thus, the specific cells may be selectively captured onto the hydrophilic polymer layer, for example, by retaining the contacted sample for a predetermined time and then washing it. Then, it can be expected that by counting the number of captured specific cells, one can determine the number of specific cells in the sampled blood or biological fluid, e.g. in order to evaluate the cancer-treating effect.

Figure 1B:
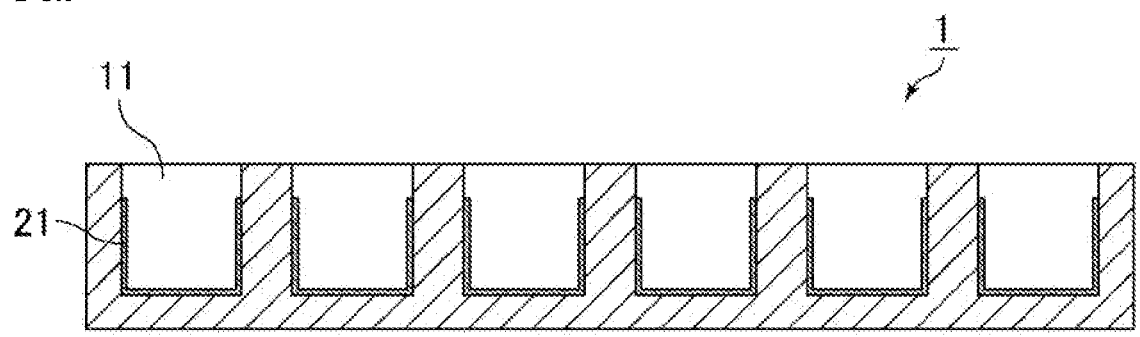

The method for capturing specific cells may be performed using, for example, a device that includes a substrate such as a multi-well plate or a chamber slide, optionally with additional components. FIG. 1A and FIG. 1B illustrate an exemplary multi-well plate 1.

The multi-well plate 1 in FIG. 1A and FIG. 1B is a device intended to capture specific cells in which wells 11 are arranged in so-called matrix form. The multi-well plate 1 has multiple wells 11 having a circular opening. The wells 11 are recesses into which a sample may be injected that is prepared by subjecting sampled blood or biological fluid to agglutination of blood cells and centrifugation to reduce the levels of blood cells such as red and white blood cells and platelets. Specific cells can be effectively captured when the injected sample is subjected to analysis as compared to when the sampled blood or biological fluid is directly subjected to analysis. Thus, it is possible to confirm the presence or absence of specific cells in the blood or biological fluid, count the number of specific cells, culture the specific cells, determine the effect of drugs, and screen the drugs.

Although FIG. 1A illustrates a 24-well plate having 24 wells 11 arranged in 4 rows by 6 columns as an example, it is sufficient for the multi-well plate 1 to have at least two wells 11, and any number of wells 11 may be provided. Examples other than the 24-well plate include general multi-well plates in which the number of wells 11 is 6, 96, 384, etc.

Each well 11 is a non-through hole which is opened at the surface of the multi-well plate 1. A sample prepared by subjecting blood or biological fluid to agglutination of blood cells and centrifugation may be injected into the wells 11 through the respective openings. If the presence of specific cells is confirmed, a culture fluid for culturing the specific cells may also be injected.

The diameter R and depth D of the opening of each well 11 are not particularly critical, and may be those of a conventional multi-well plate 1. Although in FIG. 1A and FIG. 1B, the inner side surface of each well 11 is substantially vertical to the opposite faces of the multi-well plate 1, the inner side surface of each well 11 may be inclined to taper from the opening to the bottom. Alternatively, the inner side surface may be inclined to flare out from the opening to the bottom.

Though the wells 11 in FIG. 1A and FIG. 1B are circularly opened, the openings of the wells 11 may be of any shape such as quadrangle.

The multi-well plate 1 may suitably be one in which the multiple wells 11 are separable. Since multiple wells are provided, they can be separated into wells for counting the number of specific cells and for culturing the specific cells. For example, the presence or absence of specific cells may first be confirmed in the wells for counting, and if the presence is confirmed, the specific cells may be cultured in the wells for culturing and then used to determine the effect of drugs. In a suitable chamber slide, the number of chambers is at least one but not more than ten.

In the multi-well plate 1 or chamber slide, the wells 11 preferably have a hydrophilic polymer layer formed at least partially on the inner surface thereof. In the example shown in FIG. 1A and FIG. 1B, a hydrophilic polymer layer 21 is formed on the bottom surface and a part of the side surface of the wells.

Once a sample prepared by subjecting blood or biological fluid to agglutination of blood cells and centrifugation is introduced into the wells 11, the specific cells present in the sample may be captured onto the hydrophilic polymer layer 21 while reducing adsorption of blood cells and the like. Thus, the specific cells may be selectively captured onto the hydrophilic polymer layer 21 by retaining the introduced sample for a predetermined time and then washing it.

The method for analysis of specific cells according to the present invention includes capturing specific cells such as cancer cells from blood or biological fluid as described above, and analyzing the specific cells. For example, specific cells (e.g. many types of cancer cells, including cancer cells not expressing EpCAM) may be captured by this method. Moreover, this method can sufficiently capture specific cells from blood or biological fluid while reducing adhesion or attachment of other proteins and cells, thereby selectively capturing the specific cells.

In the method for analysis of specific cells, the hydrophilic polymer layer may suitably be contacted with blood from which blood cells and the like have been removed. This can further enhance selective capture of specific cells such as cancer cells. The removal of blood cells and the like may be carried out by known techniques, such as membrane separation, as well as centrifugation as described above.

EXAMPLES

The present invention is specifically described with reference to, but not limited to, examples below.

Device Example 1

Using azobisisobutyronitrile (AIBN), 2-methoxyethyl acrylate was thermally polymerized at 80° C. for six hours to produce poly(2-methoxyethyl acrylate) (molecular weight: Mn=about 15,000, Mw=about 50,000). Then, a 1.0% solution of the poly(2-methoxyethyl acrylate) in methanol was prepared.

The poly(2-methoxyethyl acrylate) solution (1% by mass) was injected into the wells of a polystyrene 24-well plate and left for 30 minutes at room temperature. Thereafter, the solution was partly drawn using a pipette, followed by drying to prepare a medical analysis device.

Device Example 2

A medical analysis device was prepared as in Device Example 1, except that the concentration of the poly(2-methoxyethyl acrylate) solution was changed to 2.5% by mass.

Device Example 3

A medical analysis device was prepared as in Device Example 1, except that the concentration of the poly(2-methoxyethyl acrylate) solution was changed to 5.0% by mass.

Device Example 4

A medical analysis device was prepared as in Device Example 1, except that a borosilicate glass chamber slide was used, and the concentration of the poly(2-methoxyethyl acrylate) solution was changed to 0.3% by mass.

Device Example 5

A medical analysis device was prepared as in Device Example 4, except that the concentration of the poly(2-methoxyethyl acrylate) solution was changed to 0.5% by mass.

Device Example 6

A medical analysis device was prepared as in Device Example 1, except that no poly(2-methoxyethyl acrylate) solution was injected and no poly(2-methoxyethyl acrylate) layer was formed.

[Thickness of Hydrophilic Polymer Layer (Coating Layer)]

The thickness of the hydrophilic polymer layer of each of the medical analysis devices was determined by measuring (photographing) a cross section of the hydrophilic polymer layer using a TEM at an accelerating voltage of 15 kV and a magnification of 1000 times.

20 minutes at room temperature (about 23° C.). Then, the mononuclear cell layer was separated. To the separated mononuclear cell layer was added a phosphate buffer (PBS) solution, followed by centrifugation again to concentrate the mononuclear cell layer. After the centrifugation, the aggregates at the lowermost layer were suspended in a liquid medium containing 10% fetal bovine serum (FBS) in a volume equal to the initial whole blood volume. A 1 ml portion of the suspension was injected into each well and left at 37° C. for one hour to cause adhesion. Then, non-adhered cells were washed away with a PBS solution. Thereafter, the number of adhered cancer cells was counted using a fluorescence microscope.

(Method for Agglutination of Blood Cells)

To the spiked blood dilution prepared by diluting the spiked blood with an equal volume of a liquid medium was added RosetteSep Human CD45 Depletion Cocktail (STEMCELL Technologies, an antibody reagent for agglutinating red and white blood cells) at 1/20 the volume of the undiluted spiked blood. The mixture was left at room temperature for 20 minutes to cause agglutination.

TABLE 1

|  | Device Example 1 | | Device Example 2 | | Device Example 3 | |
| --- | --- | --- | --- | --- | --- | --- |
|  | Example 1 | Comparative Example 1 | Example 2 | Comparative Example 2 | Example 3 | Comparative Example 3 |
| Agglutination of blood cells | Performed | Not performed | Performed | Not performed | Performed | Not performed |
| Thickness of hydrophilic polymer layer (coating layer) (nm) | 39 | 39 | 86 | 86 | 280 | 280 |
| Contact angle with water (°) | 43 | 43 | 50 | 50 | 60 | 60 |
| Analysis of whole blood spiked with cancer cells (number of cells) | 75 | 59 | 80 | 58 | 85 | 59 |

|  | Device Example 4 | | Device Example 5 | | Device Example 6 | |
| --- | --- | --- | --- | --- | --- | --- |
|  | Example 4 | Comparative Example 4 | Example 5 | Comparative Example 5 | Comparative Example 6 | Comparative Example 7 |
| Agglutination of blood cells | Performed | Not performed | Performed | Not performed | Performed | Not performed |
| Thickness of hydrophilic polymer layer (coating layer) (nm) | 108 | 108 | 450 | 450 | 0 | 0 |
| Contact angle with water (°) | 52 | 52 | 65 | 65 | 85 | 85 |
| Analysis of whole blood spiked with cancer cells (number of cells) | 63 | 45 | 76 | 48 | 48 | 47 |

[Contact Angle with Water]

A volume of 2 µL of distilled water was dropped onto the surface of the hydrophilic polymer layer of each medical analysis device. Thirty seconds later, the contact angle was measured by the θ/2 method at room temperature.

[Analysis of Whole Blood Spiked with Cancer Cells]

Stained human colon adenocarcinoma (HT-29) cells were suspended in whole blood at a concentration of 100 cells per mL of blood to prepare spiked blood. The spiked blood was diluted with an equal volume of a liquid medium to prepare a spiked blood dilution, which was then used directly or subjected to agglutination of blood cells as described later. Next, to a 15 ml centrifuge tube were added a solution for isolation (Lymphoprep, density=1.077±0.001 g/mL) and then the spiked blood dilution or the one in which blood cells were agglutinated, followed by centrifugation at 800 G for When a sample prepared by subjecting blood or biological liquid to agglutination of blood cells and centrifugation was contacted with a hydrophilic polymer layer (coating layer), specific cells such as cancer cells were selectively captured and the number of adhered specific cells was increased.

REFERENCE SIGNS LIST 1 multi-well plate
11 well
21 hydrophilic polymer layer

The invention claimed is:

1. A method for capturing specific cells present in blood or biological fluid, the method comprising:

agglutinating blood cells in sampled blood or biological fluid;
centrifuging the resulting blood or biological fluid; and
then capturing specific cells therefrom onto a hydrophilic polymer layer;
wherein the agglutinating blood cells comprises binding and agglutinating of red blood cells and white blood cells via an antigen-antibody reaction;
wherein the specific cells are cancer cells;
wherein the capturing of specific cells is carried out in a well;
wherein the hydrophilic polymer layer is formed on at least a part of the inner surface of the well;
wherein the well is a non-through hole;
wherein the well is formed of at least one substrate selected from the group consisting of soda-lime glass, borosilicate glass, and styrene resins;
wherein the hydrophilic polymer layer is formed of at least one hydrophilic polymer selected from the group consisting of
(a) poly(meth)acryloylmorpholine,
(b) polymers represented by the following formula (I):

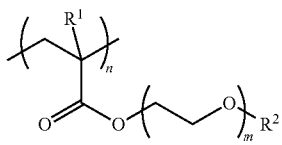

wherein $R^1$ of formula (I) represents a hydrogen atom or a methyl group, $R^2$ represents an alkyl group, m represents 1 to 5, and n represents the number of repetitions, and
(c) a copolymer of at least one hydrophilic monomer selected from the group consisting of (meth)acryloylmorpholine and compounds represented by the following formula (I-1):

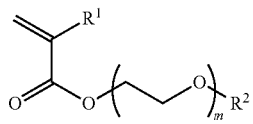

wherein $R^1$ of formula (I-1) represents a hydrogen atom or a methyl group, $R^2$ represents an alkyl group, and m represents 1 to 5, with an additional monomer; and
wherein the hydrophilic polymer layer has a thickness of 10 to 500 nm.

2. The method for capturing specific cells according to claim 1,
wherein the sampled blood or biological fluid is diluted before the agglutination and the centrifugation.

3. The method for capturing specific cells according to claim 2,
wherein a buffer solution or a liquid medium is used for the dilution.

4. The method for capturing specific cells according to claim 1,
wherein the hydrophilic polymer layer is formed of at least one hydrophilic polymer selected from the group consisting of poly(meth)acryloylmorpholine and polymers represented by the formula (I).

5. The method for capturing specific cells according to claim 1,
wherein the hydrophilic polymer layer is formed of a copolymer of at least one hydrophilic monomer selected from the group consisting of (meth)acryloylmorpholine and compounds represented by the formula (I-1).

6. The method for capturing specific cells according to claim 1,
wherein the well is formed from said styrene resin.

7. A method for analysis of specific cells, comprising capturing specific cells from blood or biological fluid by the method for capturing specific cells according to claim 1, and analyzing the specific cells.

* * * * *